(12) United States Patent
Nakazato et al.

(10) Patent No.: US 6,290,942 B1
(45) Date of Patent: Sep. 18, 2001

(54) CARBOXYL-BEARING SILICONE EMULSIONS METHOD OF MAKING AND HAIR PREPARATIONS

(75) Inventors: Morizo Nakazato; Hisashi Aoki, both of Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/320,268

(22) Filed: May 27, 1999

(30) Foreign Application Priority Data

May 28, 1998 (JP) .................................................. 10-164308

(51) Int. Cl.⁷ ..................................................... A61K 7/06
(52) U.S. Cl. .................................... 424/70.121; 424/70.1; 424/70.11; 424/70.12
(58) Field of Search ............................... 424/70.1, 70.11, 424/70.12, 70.121

(56) References Cited

U.S. PATENT DOCUMENTS

| | | |
|---|---|---|
| 3,208,911 * | 9/1965 | Oppliger . |
| 3,294,725 * | 12/1966 | Findlay et al. . |
| 3,360,491 * | 12/1967 | Axon . |
| 3,715,377 * | 2/1973 | Siciliano . |
| 4,450,152 | 5/1984 | Ona et al. . |
| 4,529,586 | 7/1985 | DeMarco et al. . |
| 4,563,347 | 1/1986 | Starch . |
| 4,597,962 | 7/1986 | Grollier et al. . |
| 4,601,902 | 7/1986 | Fridd et al. . |
| 4,749,565 | 6/1988 | Grollier . |
| 4,844,888 * | 7/1989 | Zawadzki . |
| 5,077,041 | 12/1991 | Yamashina et al. . |
| 5,160,449 | 11/1992 | Halloran . |
| 5,211,883 | 5/1993 | Yamashina et al. . |
| 5,482,703 | 1/1996 | Pings . |

FOREIGN PATENT DOCUMENTS

| | | |
|---|---|---|
| 55-66506 | 5/1980 | (JP) . |
| 56-45406 | 4/1981 | (JP) . |
| 58-74602 | 5/1983 | (JP) . |
| 58-21005 | 12/1983 | (JP) . |
| 60-36407 | 2/1985 | (JP) . |
| 60-56916 | 4/1985 | (JP) . |
| 61-6 | 1/1986 | (JP) . |
| 61-78710 | 4/1986 | (JP) . |
| 63-275515 | 11/1988 | (JP) . |
| 63-307810 | 12/1988 | (JP) . |
| 63-307811 | 12/1988 | (JP) . |
| 1-172313 | 7/1989 | (JP) . |
| 1-190619 | 7/1989 | (JP) . |
| 1-203314 | 8/1989 | (JP) . |
| 2-502286 | 7/1990 | (JP) . |
| 2-273609 | 11/1990 | (JP) . |
| 2-273612 | 11/1990 | (JP) . |
| 3-206022 | 9/1991 | (JP) . |
| 4-36225 | 2/1992 | (JP) . |
| 5-85918 | 4/1993 | (JP) . |

OTHER PUBLICATIONS

English Abstract for Japan 55–66506.
English Abstract for Japan 58–74602.
English Abstract for Japan 63–275515.
English Abstract for Japan 63–307810.
English Abstract for Japan 63–307811.
English Abstract for Japan 1–172313.
English Abstract for Japan 1–190619.
English Abstract for Japan 1–203314.
English Abstract for Japan 2–273609.
English Abstract for Japan 2–273612.
English Abstract for Japan 4–36225.
English Abstract for Japan 5–85918.

* cited by examiner

*Primary Examiner*—Thurman K Page
*Assistant Examiner*—P. E. McQueeney
(74) *Attorney, Agent, or Firm*—Millen, White, Zelano, & Branigan, P.C.

(57) ABSTRACT

The invention provides an emulsion comprising an organopolysiloxane of the formula:

$$R^1_x R^2_y R^3_z SiO_{(4-x-y-z)/2}$$

wherein $R^1$ is a monovalent $C_{1-20}$ hydrocarbon group, $R^2$ is as defined for $R^1$ or OX wherein X is hydrogen or a monovalent $C_{1-6}$ hydrocarbon group, $R^3$ is —$R^4$COOH wherein $R^4$ is a divalent $C_{1-20}$ hydrocarbon group, $0<x\leq2$, $0\leq y<0.05$, $0<z\leq0.15$, and $1.8<x+y+z<2.2$, the organopolysiloxane containing at least one carboxyl group in the molecule and having a degree of polymerization of 200–20,000. The carboxyl-bearing silicone emulsion is formulated in a hair-care product, which when applied to hair, remains adsorbed on both sound hair and damaged hair, and is effective for imparting smoothness, suppleness, antistatic property, style-holding ability, and a pleasant finish.

16 Claims, No Drawings

CARBOXYL-BEARING SILICONE EMULSIONS METHOD OF MAKING AND HAIR PREPARATIONS

This invention relates to a carboxyl-bearing silicone emulsion suitable in formulating hair preparations, a method for preparing the emulsion, and a hair preparation.

BACKGROUND OF THE INVENTION

Hair preparations comprising a conditioning component such as a cationic non-silicone polymer or cationic surfactant, in admixture with oily additives such as higher alcohols, glycerides, liquid paraffin, and esters are conventionally used for the purpose of imparting suppleness, smoothness and antistatic properties to hair. As compared with the cationic non-silicone base conditioning component used alone, blends of oily additives with the conditioning component are effective in improving suppleness and smoothness, but undesirably leave a feel of residual oil, that is, an oily or greasy sticking feel.

By contrast, silicones as typified by dimethylpolysiloxane are known to be smooth and lubricating, as compared with the above-described oily additives, and thus impart a dry feel and luster to hair. For this reason, silicones are used in many hair preparations. The silicones, however, do not have satisfactory functions of suppleness and style retention and in particular, little adsorb or remain on the hair damaged by permanent waving, coloring or bleaching, failing to exerts their full effects.

For this reason, conventional silicones must be blended in hair-care products in large amounts in order to provide satisfactory functions, with the drawback that hair base (near the scalp) and other regions where hair is less damaged feel sticky. Also blending large amounts of silicones compromises the stability of products.

Further, conventional hair-care products are not kept effective after hair washing. From this standpoint, efforts have been made to develop long-lasting hair-care products using modified silicone polymers which are more sorptive to hair. Such hair-care products are disclosed, for example, in JP-A 55-66506, 56-45406, 58-210005, 58-74602, 60-36407, 60-56916, 61-6, 61-78710, 63-275515, 63-307810, 63-307811, 1-172313, 1-190619, 1-203314, 2-273609, 2-273612, 2-502286, 3-206022, 4-36225, and 5-85918.

However, some of the hair-care products having modified silicone polymers blended therein are effective to sound hair, but fail to impart a soft and silky texture and hence, a pleasant feel to damaged hair like permanent-waved hair and split-end hair. And some other products are effective to damaged hair, but become sticky on sound hair.

Therefore, there is a demand to have a hair-care product having blended therein a silicone component capable of fully exerting its effect to both sound hair and permanent-waved or otherwise damaged hair.

SUMMARY OF THE INVENTION

An object of the invention is to provide a silicone emulsion which is formulated in a hair preparation as a silicone component, when applied to hair, remains adsorbed on hair in any state including sound hair and damaged hair, and effective for imparting smoothness, suppleness, lubricity, antistatic properties, and style-holding ability, and providing a pleasant finish and feel, while the hair preparation is shelf stable. Another object of the invention is to provide a method for preparing the silicone emulsion. A further object is to provide a hair preparation having the silicone emulsion blended therein.

In a first aspect, the invention provides a carboxyl-bearing silicone emulsion comprising an organopolysiloxane of the following general formula (1):

$$R^1_x R^2_y R^3_z SiO_{(4-x-y-z)/2} \qquad (1)$$

wherein $R^1$ is a monovalent hydrocarbon group having 1 to 20 carbon atoms, $R^2$ is as defined for $R^1$ or an OX group wherein X is hydrogen or a monovalent hydrocarbon group having 1 to 6 carbon atoms, $R^3$ is a $-R^4COOH$ group wherein $R^4$ is a divalent hydrocarbon group having 1 to 20 carbon atoms, x, y, and z are numbers satisfying $0 < x \leq 2$, $0 \leq y < 0.05$, $0 < z \leq 0.15$, and $1.8 < x+y+z < 2.2$. The organopolysiloxane contains at least one carboxyl group in the molecule and has a degree of polymerization of 200 to 20,000.

In one preferred embodiment, the organopolysiloxane of formula (1) includes
(A) structural units of the following average unit formula (2):

$$R^1_a R^2_b SiO_{(4-a-b)/2} \qquad (2)$$

wherein $R^1$ and $R^2$ are as defined above, a and b are numbers satisfying $0 < a \leq 3$, $0 \leq b < 3$, and $1 \leq a+b \leq 3$,
(B) structural units of the following average unit formula (3):

$$R^3_c R^2_d SiO_{(4-c-d)/2} \qquad (3)$$

wherein $R^2$ and $R^3$ are as defined above, c and d are numbers satisfying $0 < c \leq 3$, $0 \leq d < 3$, and $1 \leq c+d \leq 3$,
(C) structural units of the following average unit formula (4):

$$R^1 SiO_{3/2} \qquad (4)$$

wherein $R^1$ is as defined above,
in a molar ratio (A):(B):(C) of 1: (0.0001 to 0.01): (0 to 0.01).

The carboxyl-bearing silicone emulsion defined above is quite effective as a silicone component in hair preparations. More specifically, the silicone emulsified in the above-defined emulsion has carboxyl groups serving to adsorb to hair. When the emulsion is blended as a silicone component in a hair preparation, even in an ordinary amount, the silicone imparts to less damaged hair the functions inherent to silicones and at the same time, exerts its effects to damaged hair. The silicone remains highly sorptive to hair in any state, regardless of the degree of hair damage, imparts smoothness, suppleness and antistatic effect to hair, and achieves a soft, silky, dry, non-sticking, pleasant finish. Additionally, the hair preparation is resistant to overnight kinking and tangling, and able to hold style. In summary, the hair preparation having the inventive emulsion blended therein has many benefits including high retention on hair and satisfactory effects on hair independent of the degree of damage by permanent waving or heat drying while it is free of color fading or discoloration and shelf stable.

In another aspect, the invention provides a method for preparing the above-described carboxyl-bearing silicone emulsion comprising the steps of emulsion polymerizing a mixture of organopolysiloxanes in water in the presence of an anionic surfactant for emulsion polymerization, and neutralizing the resulting reaction mixture; or the steps of emulsifying and dispersing a mixture of organopolysiloxanes in water in the presence of a nonionic or anionic surfactant, emulsion polymerizing the organopolysiloxanes in the presence of a polymerization catalyst, and neutralizing the resulting reaction mixture. The mixture of organopolysiloxanes used herein contains (A) an organopolysiloxane of the following general formula (2a):

$$R^1_a R^2_b SiO_{(4-a-b)/2} \qquad (2a)$$

wherein $R^1$ and $R^2$ are as defined above, a and b are numbers satisfying $0 < a \leq 3$, $0 \leq b < 3$, and $1 \leq a+b \leq 3$, (B) an organopolysiloxane of the following general formula (3a):

$$R^3_c R^2_d SiO_{(4-c-d)/2} \qquad (3a)$$

wherein $R^2$ and $R^3$ are as defined above, c and d are numbers satisfying $0 < c \leq 3$, $0 \leq d < 3$, and $1 \leq c+d \leq 3$, and optionally, (C) an organosilane of the following general formula (4a):

$$R^1 Si(OX)_3 \qquad (4a)$$

wherein $R^1$ and X as defined above, or a partial hydrolytic condensate thereof.

In a further aspect, the invention provides a hair preparation comprising the carboxyl-bearing silicone emulsion.

DETAILED DESCRIPTION OF THE INVENTION

The carboxyl-bearing silicone emulsion of the invention is an emulsion in water of an organopolysiloxane of the following general formula (1):

$$R^1_x R^2_y R^3_z SiO_{(4-x-y-z)/2} \qquad (1)$$

wherein $R^1$ is a monovalent hydrocarbon group having 1 to 20 carbon atoms, $R^2$ is as defined for $R^1$ or an OX group wherein X is hydrogen or a monovalent hydrocarbon group having 1 to 6 carbon atoms, $R^3$ is a —$R^4$COOH group wherein $R^4$ is a divalent hydrocarbon group having 1 to 20 carbon atoms, x, y, and z are numbers satisfying $0 < x \leq 2$, $0 \leq y < 0.05$, $0 < z \leq 0.15$, and $1.8 < x+y+z < 2.2$, the organopolysiloxane containing at least one carboxyl group in the molecule and having a degree of polymerization of 200 to 20,000.

In formula (1), $R^1$ represents monovalent hydrocarbon groups having 1 to 20 carbon atoms, including unsubstituted monovalent hydrocarbon groups, for example, alkyl groups such as methyl, ethyl, propyl, butyl, octyl, lauryl, and stearyl; alkenyl groups such as vinyl and allyl; aryl groups such as phenyl, tolyl and naphthyl; aralkyl groups such as 2-phenylethyl; cycloalkyl groups such as cyclopentyl and cyclohexyl; and substituted monovalent hydrocarbon groups in which some or all of the hydrogen atoms attached to carbon atoms in the foregoing groups are replaced by halogen atoms (e.g., fluoro, chloro and bromo), cyano groups, mercapto groups or a mixture thereof, such as 3,3,3-trifluoropropyl, cyanopropyl and mercaptopropyl. Of these, those groups of 1 to 6 carbon atoms are preferable, and methyl, ethyl, propyl and phenyl are more preferable, with methyl and phenyl being most preferable.

$R^2$ is as defined for $R^1$ or an OX group wherein X is hydrogen or a monovalent hydrocarbon group having 1 to 6 carbon atoms. Examples of the monovalent hydrocarbon group of 1 to 6 carbon atoms represented by X include unsubstituted monovalent hydrocarbon groups, for example, alkyl groups such as methyl, ethyl, propyl, and butyl; alkenyl groups such as vinyl and allyl; and aryl groups such as phenyl; and substituted monovalent hydrocarbon groups in which some or all of the hydrogen atoms attached to carbon atoms in the foregoing groups are replaced by halogen atoms (e.g., fluoro, chloro and bromo), cyano groups, mercapto groups or a mixture thereof, such as 3,3,3-trifluoropropyl, cyanopropyl and mercaptopropyl.

$R^3$ is a —$R^4$COOH group wherein $R^4$ is a divalent hydrocarbon group having 1 to 20 carbon atoms. Examples of the divalent hydrocarbon group of 1 to 20 carbon atoms represented by $R^4$ include alkylene groups such as methylene, ethylene, trimethylene, tetramethylene and hexamethylene; and phenylene groups. Of these, ethylene and trimethylene are preferable.

Letters x, y, and z are numbers satisfying $0 < x \leq 2$, preferably $1.8 \leq x \leq 2$, $0 \leq y < 0.05$, preferably $0 \leq y \leq 0.01$, $0 < z \leq 0.15$, preferably $0.01 \leq z \leq 0.05$, and $1.8 < x+y+z < 2.2$, preferably $1.81 \leq x+y+z \leq 2.06$.

The carboxyl-bearing organopolysiloxane of formula (1) is comprised of structural units (A) and (B), and optionally, structural units (C), shown below.

(A) structural units of the following average unit formula (2):

$$R^1_a R^2_b SiO_{(4-a-b)/2} \qquad (2)$$

$R^1$ and $R^2$ are as defined above, a and b are numbers satisfying $0 < a \leq 3$, $0 \leq b < 3$, and $1 \leq a+b \leq 3$.

(B) structural units of the following average unit formula (3):

$$R^3_c R^2_d SiO_{(4-c-d)/2} \qquad (3)$$

$R^2$ and $R^3$ are as defined above, c and d are numbers satisfying $0 < c \leq 3$, $0 \leq d < 3$, and $1 \leq c+d \leq 3$.

(C) structural units of the following average unit formula (4):

$$R^1 SiO_{3/2} \qquad (4)$$

$R^1$ is as defined above.

Illustrative examples of structural unit (A) are [(CH$_3$)$_2$SiO], [(CH$_3$)(C$_6$H$_5$)SiO], [(C$_6$H$_5$)$_2$SiO], [(C$_2$H$_5$)$_2$SiO], [(CH$_3$)(C$_2$H$_5$)SiO], [(C$_3$H$_7$)$_2$SiO], and [(CH$_3$)(C$_3$H$_7$)SiO].

Illustrative examples of structural unit (B) are [(CH$_3$)(HOOCC$_2$H$_4$)SiO], [(CH$_3$)(HOOCC$_3$H$_6$)SiO], and [(CH$_3$)(HOOCC$_{11}$H$_{22}$)SiO].

Illustrative examples of structural unit (C) are [CH$_3$SiO$_{3/2}$], [C$_6$H$_5$SiO$_{3/2}$], [C$_2$H$_5$SiO$_{3/2}$], and [C$_3$H$_7$SiO$_{3/2}$].

For the carboxyl-bearing organopolysiloxane of formula (1), it suffices that structural units (A) and (B) and optionally (C) are contained. The order of bonding of these units is not limited, and they may be bonded to form block or random copolymers, for example.

The carboxyl-bearing organopolysiloxane of formula (1) preferably contains structural units (A), (B) and (C) in a molar ratio (A):(B):(C) of 1: (0.0001 to 0.01): (0 to 0.01), more preferably 1: (0.0005 to 0.008): (0 to 0.005). With less than 0.0001 mol of structural units (B) per mol of structural units (A), the silicone would lose retentivity on hair and impart poor smoothness. With more than 0.01 mol of (B) per mol of (A), the silicone would impart poor suppleness to hair. With more than 0.01 mol of structural units (C) per mol of structural units (A), the silicone would cause a somewhat stiff feel. The lower limit of structural units (C), if any, may be 0.0001 mol per mol of (A).

It is understood that the organopolysiloxane of formula (1) may further contain other structural units such as $SiO_{4/2}$ in addition to structural units (A), (B) and (C) insofar as the objects of the invention are not impaired.

The carboxyl-bearing organopolysiloxane of formula (1) has an average degree of polymerization of 200 to 20,000, especially 1,000 to 10,000. Organopolysiloxanes with an average degree of polymerization of less than 200 have poor conditioning effects whereas organopolysiloxanes with an average degree of polymerization of more than 20,000 cause a parched or sticky feel.

In the emulsion of the invention, a nonionic or anionic surfactant may be contained in an amount of 0.5 to 50 parts by weight per 100 parts by weight of the organopolysiloxane of formula (1).

According to the invention, the carboxyl-bearing silicone emulsion can be prepared by emulsion polymerizing a mixture of organopolysiloxanes in water in the presence of an anionic surfactant for emulsion polymerization, and neutralizing the resulting reaction mixture; or by emulsifying and dispersing a mixture of organopolysiloxanes in water in the presence of a nonionic or anionic surfactant, emulsion polymerizing the organopolysiloxanes in the presence of a polymerization catalyst, and neutralizing the resulting reaction mixture. The mixture of organopolysiloxanes used herein contains (A) an organopolysiloxane of the following general formula (2a):

$$R^1_a R^2_b SiO_{(4-a-b)/2} \quad (2a)$$

wherein $R^1$ and $R^2$ are as defined above, a and b are numbers satisfying $0 < a \leq 3$, $0 \leq b < 3$, and $1 \leq a+b \leq 3$, (B) an organopolysiloxane of the following general formula (3a):

$$R^3_c R^2_d SiO_{(4-c-d)/2} \quad (3a)$$

wherein $R^2$ and $R^3$ are as defined above, c and d are numbers satisfying $0 < c \leq 3$, $0 \leq d < 3$, and $1 \leq c+d \leq 3$, and optionally, (C) an organosilane of the following general formula (4a):

$$R^1 Si(OX)_3 \quad (4a)$$

wherein $R^1$ and X as defined above, or a partial hydrolytic condensate thereof.

Exemplary of organopolysiloxane (A) is octamethyltetrasiloxane. Exemplary of organopolysiloxane (B) is tetracarboxypropyltetramethylcyclotetrasiloxane. Exemplary of organosilane (C) is methyltriethoxysilane.

The above components (A), (B) and (C) are preferably blended such that the molar ratio of structural units (A), (B) and (C) may fall in the range of (A):(B):(C)=1 (0.0001 to 0.01): (0 to 0.01) as described above.

In the first method, the carboxyl-bearing silicone emulsion can be prepared by emulsion polymerizing a mixture of organopolysiloxanes in water in the presence of an anionic surfactant for emulsion polymerization, and neutralizing the resulting reaction mixture.

The emulsion polymerization-promoting anionic surfactant is preferably selected from aliphatically substituted benzenesulfonic acids of the general formula (5):

$$R^5 C_6 H_4 SO_3 H \quad (5)$$

wherein $R^5$ is a monovalent aliphatic hydrocarbon group having at least 6 carbon atoms, and aliphatic hydrogen sulfates of the general formula (6):

$$R^6 OSO_2 H \quad (6)$$

wherein $R^6$ is a monovalent aliphatic hydrocarbon group having at least 6 carbon atoms. In formulae (5) and (6), $R^5$ and $R^6$ represent monovalent aliphatic hydrocarbon groups having at least 6 carbon atoms, preferably 6 to 18 carbon atoms, for example, hexyl, octyl, decyl, dodecyl, cetyl, stearyl, myricyl, oleyl, nonenyl, octynyl, phytyl, and pentadecadienyl.

Illustrative examples of the emulsion polymerization-promoting anionic surfactants represented by formulae (5) and (6) include hexylbenzenesulfonic acid, octylbenzenesulfonic acid, dodecylbenzenesulfonic acid, cetylbenzenesulfonic acid, octyl sulfate, lauryl sulfate, oleyl sulfate, and cetyl sulfate.

The amount of the emulsion polymerization-promoting anionic surfactant used is preferably about 2 to 80 parts, more preferably about 5 to 50 parts by weight per 100 parts by weight of the mixture of low-molecular-weight organopolysiloxanes, that is, organopolysiloxanes (A) and (B) and optionally organosilane or partial hydrolytic condensate thereof (C). With less than 2 parts of the anionic surfactant, the resulting emulsion would be unstable and separate. With more than 80 parts of the anionic surfactant, the resulting emulsion would become too thick and lose flow.

If the anionic surfactant has weak catalysis, it is used in combination with a polymerization catalyst. In this case (or second method), the carboxyl-bearing silicone emulsion can be prepared by emulsifying and dispersing a mixture of low-molecular-weight organopolysiloxanes in water in the presence of an anionic surfactant, emulsion polymerizing the organopolysiloxanes in the presence of a polymerization catalyst, and neutralizing the resulting reaction mixture.

The anionic surfactants used herein include sodium, potassium and ammonium salts of aliphatically substituted benzenesulfonic acids and aliphatic hydrogen sulfates of formulae (5) and (6), for example, sodium dodecylbenzenesulfonate, sodium octylbenzenesulfonate, ammonium dodecylbenzenesulfonate, ammonium lauryl sulfate, triethanolamine lauryl sulfate, and sodium lauryl sulfate.

Besides the anionic surfactants of formula (5) and (6), use may be made of polyoxyethylene alkyl ether sulfuric acid esters or salts thereof such as polyoxyethylene(4) lauryl ether sulfuric acid, polyoxyethylene (13) cetyl ether sulfuric acid, polyoxyethylene(6) stearyl ether sulfuric acid, polyoxyethylene(4) lauryl sodium sulfate, and polyoxyethylene(4) octyl phenyl ether ammonium sulfate; polyoxyethylene alkyl ether carboxylic acid esters or salts such as polyoxyethylene(3) lauryl ether carboxylic acid, polyoxyethylene(3) stearyl ether carboxylic acid, polyoxyethylene(6) lauryl ether sodium carboxylate, and polyoxyethylene(6) octyl ether sodium carboxylate, and mixtures thereof. The surfactant is not limited to these examples.

Since the silicone emulsion of the invention is used as shampoos for human hair and animal fur, use is also preferably made of aliphatic alcohols or aliphatic alcohol ethoxylates, especially derivatives of lauryl and myristyl alcohols and salts thereof, for example, sodium lauryl sulfate, sodium lauryl ether sulfate, ammonium lauryl sulfate, triethanol amine lauryl sulfate, monoethanolamine lauryl sulfate, disodium lauryl ethoxysulfosuccinate, and disodium cocomonoethanolamide ethoxysulfosuccinate.

The amount of the anionic surfactant used is preferably about 2 to 80 parts, more preferably about 5 to 50 parts by weight per 100 parts by weight of the mixture of low-molecular-weight organopolysiloxanes, that is, organopolysiloxanes (A) and (B) and optionally organosilane or partial hydrolytic condensate thereof (C). With less than 2 parts of the anionic surfactant, the resulting emulsion would be unstable and separate. With more than 80 parts of the anionic surfactant, the resulting emulsion would become too thick and lose flow.

As the polymerization catalyst used in combination with the anionic surfactant, use is preferably made of acidic catalysts commonly used as a polymerization catalyst for low-molecular-weight organopolysiloxanes, such as aliphatically substituted benzenesulfonic acids, aliphatic hydrogen sulfates, hydrochloric acid, sulfuric acid, and phosphoric acid. The catalyst is not limited to these examples, and any of catalysts capable of promoting polymerization of low-molecular-weight organopolysiloxanes in the presence of water may be used.

When the polymerization catalyst is used in combination, its amount is preferably about 0.1 to 20 parts by weight per 100 parts by weight of the mixture of low-molecular-weight organopolysiloxanes although the amount is not critical.

Further, for improving the stability of the emulsion, a nonionic surfactant may be used in combination with the above-described emulsion polymerization-promoting anionic surfactant or less catalytic anionic surfactant insofar as the objects of the invention are not impaired.

The nonionic surfactants used herein are preferably those having a HLB of 6 to 20, for example, polyoxyethylene(6) sorbitan monolaurate, polyoxyethylene(20) sorbitan monopalmitate, polyoxyethylene(20) sorbitan monostearate, polyoxyethylene(20) sorbitan trioleate, polyoxyethylene(6) lauryl ether, polyoxyethylene(7) cetyl ether, polyoxyethylene(12) stearyl ether, polyoxy-ethylene(9) octyl phenyl ether, polyoxyethylene(11) nonyl phenyl ether, polyethylene glycol(14) monostearate, polyethylene glycol (80) distearate, and polyoxyethylene(25) hardened castor oil, though the nonionic surfactants are not limited thereto.

An appropriate amount of the nonionic surfactant used is 0 to 50 parts by weight per 100 parts by weight of the emulsion polymerization-promoting anionic surfactant. More than 50 parts of the nonionic surfactant would deactivate the polymerization catalyst.

In an alternative of the second method, a nonionic surfactant having weak catalysis may be used in combination with a polymerization catalyst. That is, the carboxyl-bearing silicone emulsion can be prepared by emulsifying and dispersing a mixture of low-molecular-weight organopolysiloxanes in water in the presence of a nonionic surfactant, emulsion polymerizing the organopolysiloxanes in the presence of a polymerization catalyst, and neutralizing the resulting reaction mixture.

Examples of the nonionic surfactant used herein include polyoxyethylene alkyl ethers, polyoxyethylene alkyl phenyl ethers, polyoxyethylene alkyl esters, sorbitan fatty acid esters, polyoxyethylene sorbitan fatty acid esters, and sucrose fatty acid esters. Especially preferred are polyoxyethylene lauryl ether, polyoxyethylene myristyl ether, polyoxyethylene cetyl ether, polyoxyethylene tridecyl ether, polyoxyethylene oleyl ether, and polyoxyethylene stearyl ether. The molar number of ethylene oxide units added is preferably 3 to 50 mol on the average.

For the stability of the resulting emulsion, an appropriate amount of the nonionic surfactant used is about 0.5 to 50 parts, especially about 0.5 to 2 parts by weight per 100 parts by weight of the mixture of low-molecular-weight organopolysiloxanes.

Examples of the polymerization catalyst used in combination with the nonionic surfactant are the same as exemplified for the polymerization catalyst used in combination with the anionic surfactant. An appropriate amount of the polymerization catalyst used is about 0.1 to 10 parts by weight per 100 parts by weight of the mixture of low-molecular-weight organopolysiloxanes although the catalyst amount is not critical.

According to the invention, the reactants including low-molecular-weight organopolysiloxanes are emulsified, dispersed and polymerized in water. The amount of water used is not critical although about 40 to 1,900 parts, especially about 60 to 900 parts by weight of water is preferably used per 100 parts by weight of the mixture of low-molecular-weight organopolysiloxanes. With less than 40 parts of water on this basis, the organopolysiloxanes which are hydrophobic fluids occupy a greater proportion, sometimes preventing the emulsion from phase conversion from W/O to O/W so that water might not form a continuous phase. With more than 1,900 parts of water, the concentration of organopolysiloxanes becomes too low, sometimes leading to inefficient emulsification.

The initial emulsion may be prepared by conventional methods, for example, by uniformly dissolving low-molecular-weight organopolysiloxanes, adding a surfactant and optionally, a polymerization catalyst and water, and effecting emulsification, dispersion, and homogenization in a dispersing machine capable of shearing action.

The dispersing machine capable of shearing action may be selected from well-known machines which are commonly used in emulsifying and dispersing silicone fluid and operate under either high or low pressure. Exemplary dispersing machines are homomixers, colloid mills, combination mixers, sand grinder mills, agitator/homomixers, and Gaulin homogenizers though not limited thereto. Preferably the dispersing machine operates under a pressure of about 1 to 50 kg/cm$^2$.

After the low-molecular-weight organopolysiloxanes are emulsified and dispersed with the aid of the anionic or nonionic surfactant, the organopolysiloxanes are emulsion polymerized in the presence of a polymerization catalyst. Specifically, the polymerization catalyst is added to the emulsified dispersion resulting from the previous step, and with stirring, polymerization is effected at a suitable temperature of 20 to 80° C. for several hours to one week. After the completion of polymerization, the reaction mixture is neutralized, for example, with organic or inorganic alkaline substances such as sodium carbonate and amines.

The thus obtained carboxyl-bearing silicone emulsion according to the invention gives a non-flowing gel-like appearance when dried. The silicone preferably has a weight average molecular weight of about 100,000 to about 700,000, especially about 150,000 to about 500,000 though not limited thereto.

From the industrial standpoint, the emulsion should preferably contain about 1 to about 90%, more preferably about 10 to about 70%, and most preferably about 20 to about 50% by weight of the carboxyl-bearing silicone as solids.

By blending the carboxyl-bearing silicone emulsion according to the invention as a silicone component, there is obtained a hair preparation or hair-care product. From the economical standpoint, the hair preparation preferably contains about 0.001 to about 30%, more preferably about 0.1 to about 20%, further preferably about 0.1 to about 10%, most preferably about 0.1 to about 2% by weight of the carboxyl-bearing silicone emulsion, calculated as solids, and based on the entire composition. Less than 0.001% of the carboxyl-bearing silicone would be ineffective whereas formulating more than 30% of the silicone would achieve little further effects and is sometimes uneconomical.

In the hair preparation, there may be blended other silicone derivatives in addition to the essential carboxyl-bearing silicone emulsion according to the invention because the functions of silicones can be enhanced in a synergistic manner. Such useful silicone derivatives include dimethylpolysiloxane, methylphenylpolysiloxane, polyether-modified silicones, epoxy-modified silicones, fluorine-modified silicones, alcohol-modified silicones, alkyl-modified silicones, alkoxy-modified silicones, and tri-methylsiloxysilicic acid. These silicone derivatives may be used individually as such, or as a premix of two or more. Alternatively, the silicone derivatives are used as micro-dispersions or silicone emulsions in an aqueous medium, combined with one or more surfactants serving as the emulsifying agent, for example, nonionic or anionic surfactants. The silicone emulsions may be obtained by agitating/mixing methods or emulsion polymerization methods. These silicone emulsions are commercially available under the trade name of KM880, KM883, KM884, KM885, KM886, KM887, KM901, KM902, KM903, KM904, KM871P, Polon MF11C, Polon MF18, and KM4702 from Shin-Etsu Chemical Industry Co., Ltd. Of these silicone derivatives, dimethylpolysiloxane and polyether-modified silicones are preferable. When these silicone derivatives are blended in the hair preparations, an appropriate content is about 0.01 to 20%, more preferably about 0.1 to 10% by weight based on the entire composition.

In addition to the above-described components, the hair preparation of the invention may contain ingredients used in conventional hair preparations, for example, pearling agents, emulsifiers, fragrance, pigments, preservatives, antioxidants, thickeners, as well as medicaments such as dandruff control agents, antibacterial agents, anti-inflammatory agents, and vitamins, UV absorbers, and other additives as described in Encyclopedia of Shampoo Ingredients, Micelle Press, 1985. These ingredients are blended in conventional amounts not compromising the effects of the invention.

The hair preparation of the invention may be formulated in a conventional way into various hair-care products including hair shampoos, hair rinse-in shampoos, hair rinses, hair treatments, styling preparations, permanent-waving preparations, and hair dyes.

The carboxyl-bearing silicone emulsion of the invention, when blended in an ordinary amount as a silicone component in a hair preparation, imparts to less damaged hair the functions inherent to silicones and at the same time, exerts its effects to damaged hair. The silicone remains highly sorptive to hair in any state, regardless of the degree of hair damage, imparts smoothness, suppleness and antistatic effect thereto, and achieves a soft, silky, free-flowing, non-sticking, pleasant finish. Additionally, the silicone is resistant to overnight kinking and curling, and able to hold style. In summary, the inventive silicone emulsion has many benefits including high retentivity on hair and full effects on hair independent of the degree of damage by permanent waving or heat drying while it is free of color fading or discoloration and shelf stable. Therefore, the hair preparation having the inventive emulsion blended therein has all the above-described advantages and provides a nice finish to hair. The method of the invention is capable of manufacturing the carboxyl-bearing silicone emulsion in a commercially advantageous manner.

EXAMPLE

Examples of the invention are given below by way of Illustration and not by way of limitation.

Example 1

Synthesis of Carboxyl-bearing Silicone Emulsion

A carboxyl-bearing silicone emulsion was prepared by the following procedure using the following components.

| | Component | Amount |
|---|---|---|
| (a) | octamethylcyclotetrasiloxane | 500 g |
| (b) | tetracarboxypropyltetramethyl-cyclotetrasiloxane | 1.6 g |
| (c) | methyltriethoxysilane | 1.2 g |
| (d) | sodium lauryl sulfate | 10.0 g |
| (e) | polyoxyethylene lauryl ether (EO23) | 3.0 g |
| (f) | polyoxyethylene lauryl ether (EO4) | 3.0 g |
| (g) | hydrochloric acid | 0.7 g |
| (h) | sodium carbonate | 2.0 g |

In a 2-liter glass beaker, components (a), (b) and (c) were admitted and uniformly dissolved by means of a homomixer. Components (d), (e) and (f) and 480.5 g of purified water were added to the beaker and uniformly emulsified and dispersed. Component (g) was added to the resulting emulsion, which was subjected to polymerization reaction by heating at 70° C. for 72 hours. Component (h) was added to the reaction solution for neutralization, obtaining a carboxyl-bearing silicone emulsion. This carboxyl-bearing silicone contained structural units (A), (B) and (C) shown below in a molar ratio of (A):(B):(C)=1:0.001:0.001 and had a degree of polymerization of 6,000.

(A) $[(CH_3)_2SiO]$ (B) $[(CH_3)(HOOCC_{11}H_{22})SiO]$ (C) $[(CH_3)SiO_{3/2}]$

When the emulsion was heat dried at 105° C. for 3 hours, the residue in the form of a non-flowing white gel-like mass was 45% by weight. When the emulsion was allowed to stand for one month in a thermostat tank set at 50° C., it remained stable without separation.

Example 2

Synthesis of Carboxyl-bearing Silicone Emulsion

A carboxyl-bearing silicone emulsion was prepared by the same procedure as in Example 1 except that component (c) was omitted. This carboxyl-bearing silicone contained structural units (A) and (B) in a molar ratio of (A):(B)=1:0.001 and had a degree of polymerization of 2,000. When the emulsion was heat dried at 105° C. for 3 hours, the residue was 45% by weight. It was a viscous liquid having a viscosity of 1,200,000 centipoise at 25° C. When the emulsion was allowed to stand for one month in a thermostat tank set at 50° C., it remained stable without separation.

Example 3

Synthesis of Carboxyl-bearing Silicone Emulsion

A carboxyl-bearing silicone emulsion was prepared by the same procedure as in Example 1 except that the amount of component (b) was changed to 16 g and component (c) was omitted. This carboxyl-bearing silicone contained structural units (A) and (B) in a molar ratio of (A):(B)=1:0.01 and had a degree of polymerization of 1,000. When the emulsion was heat dried at 105° C. for 3 hours, the residue was 44% by weight. It was a viscous liquid having a viscosity of 600,000 centipoise at 25° C. When the emulsion was allowed to stand for one month in a thermostat tank set at 50° C., it remained stable without separation.

Examples 4–8

Comparative Examples 1–3:

Hair Shampoo

A hair shampoo base of the composition shown below was prepared. To this shampoo base, each of the carboxyl-bearing silicone emulsions obtained in Examples 1 to 3 or comparative silicones was added as shown in Table 1. The ingredients were agitated and mixed to form hair shampoo compositions.

The hair shampoo compositions were examined for tactile attributes by applying to hair. The tactile attributes examined are smoothness and finger combing, suppleness, soft and silky feel, antistatic property, non-stickiness, retentivity, resistance to overnight kinking, style-holding ability, and uniformity to the touch. The test methods are described below. The results are shown in

TABLE 1

| Hair shampoo base composition: | wt % |
|---|---|
| sodium polyoxyethylene (EO:3) lauryl sulfate (30% in water) | 30.0 |
| diethanolamide lauryl sulfate | 4.0 |
| propylene glycol | 2.0 |
| preservative, colorant, fragrance | appropriate |
| purified water | balance |
| total | 100 wt % |

Comparative silicones (CS):
CS1: dimethylpolysiloxane high polymer KM901 by Shin-Etsu Chemical Industry Co., Ltd.
CS2: dimethylpolysiloxane high polymer KM904 by Shin-Etsu Chemical Industry Co., Ltd.
CS3: aminopolysiloxane high polymer SM8702C by Toray-Dow Corning Silicone K.K.

Tests (1) Smoothness and Finger Combing, Suppleness, Soft and Silky Feel, Antistatic Property, and Stickiness A hair bundle consisted of 20 g of Japanese woman hair (length 15 cm) which had not been subject to hairdressing treatment such as cold permanent waving. Each hair shampoo, 1 or 2 g, was applied to the hair bundle, which was manipulated in an ordinary manner and finally dried. A panel of specialists made sensory evaluation on the hair bundle.

Smoothness and Finger Combing

○: very smooth touch and very good finger combing
Δ: smooth touch and good finger combing
X: rough touch and difficult finger combing

Suppleness

○: fully supple
Δ: somewhat supple
X: not supple

Soft and Silky Feel

○: fully soft and silky
Δ: somewhat short
X: not soft or silky

Antistatic Property

○: no hair fly on brushing
Δ: some hair fly on brushing
X: hair fly on brushing (2) Retentivity on Hair The hair bundle treated with each hair shampoo was further washed three times using a plain shampoo consisting of 15% by weight of sodium polyoxyethylene (3) lauryl ether sulfate, 3% by weight of diethanolamlde laurate, and the balance of deionized water and adjusted at pH 7 with citric acid. After drying, a sensory test was made on the hair bundle for examining retentivity.

○: feel residues
Δ: feel some residues
X: feel no residues (3) Resistance to Overnight Kinking, Style-holding Ability, and Uniformity to the Touch A panel of ten specialists used each hair shampoo for 2 or 3 days and made a sensory test. In the panel, two had long straight hair, two long wavy hair, two semi-long straight hair, two semi-long wavy hair, one short straight hair, and one short wavy hair.

Rating point:
+1 effective
+0.5 somewhat effective
0 not effective

Resistance to Overnight Kinking

○: resistant to overnight kinking (point 6 to 10)
Δ: less resistant to overnight kinking (point 3 to <6)
X: overnight kinking or snarling (point 0 to <3)

Style-holding Ability

○: able to hold style (points 6 to 10)
Δ: fairly hold style (point 3 to <6)
X: poorly hold style (point 0 to <3)

Uniformity to the Touch

○: uniform touch from hair base to end (point 6 to 10)
Δ: fairly uniform touch from hair base to end (point 3 to <6)
X: non-uniform touch from hair base to end (point 0 to <3)

TABLE 1

| | Example | | | | | Comparative Example | | |
|---|---|---|---|---|---|---|---|---|
| Composition (wt %) | 4 | 5 | 6 | 7 | 8 | 1 | 2 | 3 |
| Shampoo base | 95 | 95 | 95 | 95 | 95 | 95 | 95 | 95 |
| Silicone | | | | | | | | |
| Example 1 | 5 | | | 4 | | | | |
| Example 2 | | 5 | | | 4 | | | |
| Example 3 | | | 5 | | | | | |
| CS1 | | | | | | 1 | 5 | |
| CS2 | | | | | | 1 | | 5 |
| CS3 | | | | | | | | 5 |
| Smoothness | ○ | ○ | ○ | ○ | ○ | Δ | Δ | Δ |
| Suppleness | ○ | ○ | ○ | ○ | ○ | Δ | Δ | Δ |
| Silky feel | ○ | ○ | ○ | ○ | ○ | ○ | ○ | X |
| Antistatic | ○ | ○ | ○ | ○ | ○ | Δ | Δ | X |

TABLE 1-continued

|  | Example |  |  |  |  | Comparative Example |  |  |
|---|---|---|---|---|---|---|---|---|
| Composition (wt %) | 4 | 5 | 6 | 7 | 8 | 1 | 2 | 3 |
| Stickiness | nil | nil | nil | nil | nil | nil | nil | nil |
| Retentivity | ○ | ○ | ○ | ○ | ○ | X | Δ | Δ |
| Resistance to overnight kinking | ○ | ○ | ○ | ○ | ○ | Δ | Δ | Δ |
| Style-holding ability | ○ | ○ | ○ | ○ | ○ | ○ | Δ | Δ |
| Uniformity to the touch | ○ | ○ | ○ | ○ | ○ | ○ | ○ | X |

Examples 9–13

Comparative Example 4–6

Hair Rinse

A hair rinse base of the composition shown below was prepared. To this rinse base, each of the carboxyl-bearing silicone emulsions obtained in Examples 1 to 3 or the comparative silicones was added. The ingredients were agitated and mixed to form hair rinse compositions. They were examined by the same tests as in above Examples, with the results shown in Table 2.

TABLE 2

| Hair rinse base Composition: | wt % |
|---|---|
| liquid paraffin | 1.5 |
| cetyl alcohol | 2.0 |
| stearyl alcohol | 1.5 |
| stearyltrimethyl ammonium chloride | 1.0 |
| glycerol | 4.0 |
| hydroxycellulose | 1.0 |
| preservative, colorant, fragrance | appropriate |
| purified water | 89.0 |
| total | 100 wt % |

|  | Example |  |  |  |  | Comparative Example |  |  |
|---|---|---|---|---|---|---|---|---|
| Composition (wt %) | 4 | 5 | 6 | 7 | 8 | 1 | 2 | 3 |
| Shampoo base | 95 | 95 | 95 | 95 | 95 | 95 | 95 | 95 |
| Silicone |  |  |  |  |  |  |  |  |
| Example 1 | 5 |  |  | 4 |  |  |  |  |
| Example 2 |  | 5 |  |  | 4 |  |  |  |
| Example 3 |  |  | 5 |  |  |  |  |  |
| CS1 |  |  |  | 1 |  | 5 |  |  |
| CS2 |  |  |  |  | 1 |  | 5 |  |
| CS3 |  |  |  |  |  |  |  | 5 |
| Smoothness | ○ | ○ | ○ | ○ | ○ | Δ | Δ | Δ |
| Suppleness | ○ | ○ | ○ | ○ | ○ | Δ | Δ | Δ |
| Silky feel | ○ | ○ | ○ | ○ | ○ | Δ | Δ | Δ |
| Antistatic | ○ | ○ | ○ | ○ | ○ | Δ | Δ | ○ |
| Stickiness | nil | nil | nil | nil | nil | nil | nil | nil |
| Retentivity | ○ | ○ | ○ | ○ | ○ | X | Δ | ○ |
| Resistance to overnight kinking | ○ | ○ | ○ | ○ | ○ | Δ | Δ | Δ |
| Style-holding ability | ○ | ○ | ○ | ○ | ○ | X | Δ | X |
| Uniformity to the touch | ○ | ○ | ○ | ○ | ○ | Δ | Δ | X |

Example 14

Styling Lotion

A styling lotion of the following composition was prepared by a conventional procedure. When applied to hair, this styling lotion imparted smoothness, suppleness, antistatic effect, a good finish, resistance to overnight kinking, and style-holding ability to hair and was left more attached to hair.

| N-(2-dodecyl)hexadecyl-N,N,N-trimethylammonium chloride | 1.5wt% |
|---|---|
| Polyethylene glycol | 0.5 |
| Carboxyl-bearing silicone (Example 2) | 8.0 |
| Dimethylpolysiloxane (50000 cp) | 0.5 |
| acrylic resin in alkanol amine | 5.0 |
| Polyethylene glycol | 1.0 |
| Methacrylate polymer | 1.0 |
| Ethanol | 20.0 |
| Fragrance | 0.3 |
| Water | balance |
| total | 100 wt % |

Example 15

Conditioning Foam

A conditioning foam of the following composition was prepared by a conventional procedure. When applied to hair, this conditioning foam imparted smoothness, suppleness, antistatic effect, a good finish, resistance to overnight kinking, and style-holding ability to hair and was left more attached to hair.

| N-(2-decyl)tetradecyl-N,N,N-trimethylammonium chloride | 1.5wt% |
|---|---|
| Octyl dodecyl myristate | 1.0 |
| Dipropylene glycol | 1.0 |
| Carboxyl-bearing silicone (Example 2) | 5.0 |
| Polyether-modified silicone (KF6005, Shin-Etsu Chemical Industry Co., Ltd.) | 0.5 |
| Glycerol | 2.5 |
| Liquid paraffin | 2.5 |
| pentaerythritol isostearyl with 1 mol glycidyl ether added | 1.0 |
| Ethanol | 5.0 |
| Methylparaben | 0.2 |
| Fragrance | 0.1 |
| Propellant (LPG) | 10.0 |
| Water | balance |
| total | 100 wt % |

Example 16

Permanent Waving Preparation

A first permanent waving preparation of the following composition was prepared by a conventional procedure. When applied to hair, this preparation imparted smoothness, suppleness, antistatic effect, a good finish, resistance to overnight kinking, and style-holding ability to hair and was left more attached to hair.

| Ammonium thioglycolate | 6.0wt% |
|---|---|
| Carboxyl-bearing silicone (Example 1) | 1.0 |
| Aqueous ammonia | 3.0 |
| Frost DS (disodium EDTA) | 0.5 |
| Benzyl alcohol | 10.0 |

-continued

| | |
|---|---|
| N-(2-decyl)tetradecyl-N,N,N-trimethylammonium chloride | 1.5 |
| Water | balance |
| total | 100 wt % |

Example 17

Permanent Waving Preparation

A second permanent waving preparation of the following composition was prepared by a conventional procedure. When applied to hair, this preparation imparted smoothness, suppleness, antistatic effect, a good finish, resistance to overnight kinking, and style-holding ability to hair and was left more attached to hair.

| | |
|---|---|
| Sodium bromate | 8.0wt% |
| N-(2-dodecyl)hexadecyl-N,N,N-trimethylammonium chloride | 1.5 |
| Dimethylpolysiloxane (200 cs) | 5.0 |
| Carboxyl-bearing silicone (Example 1) | 0.5 |
| Water | balance |
| total | 100 wt % |

Example 18

Hair Treatment

A hair treatment of the following composition was prepared by a conventional procedure. When applied to hair, this hair treatment imparted smoothness, suppleness, antistatic effect, a good finish, resistance to overnight kinking, and style-holding ability to hair and was left more attached to hair.

| | |
|---|---|
| 2-dodecylhexadecyltrimethylammonium chloride | 1.5wt% |
| Stearyltrimethylammonium chloride | 2.0 |
| Sedostearyl alcohol | 3.0 |
| Oleic acid monoglyceride | 1.0 |
| Benzyl alcohol | 5.0 |
| Carboxyl-bearing silicone (Example 2) | 3.0 |
| Hydroxyethyl cellulose (1% aqueous solution, 8000 cp) | 0.5 |
| Methylparaben | 0.2 |
| Fragrance | 0.4 |
| Water | balance |
| total | 100 wt % |

Example 19

Hair Conditioner

A hair conditioner of the following composition was prepared by a conventional procedure. When applied to hair, this hair conditioner imparted smoothness, suppleness, antistatic effect, a good finish, resistance to overnight kinking, and style-holding ability to hair and was left more attached to hair.

| | |
|---|---|
| Di (2-hexadecyl)dimethylammonium chloride | 0.5 wt% |
| Methylphenylpolysiloxane (300 cs) | 1.0 |
| Dipropylene glycol | 1.0 |
| Carboxyl-bearing silicone (Example 1) | 0.01 |
| Stearic acid monoglyceride | 1.0 |
| Glycerol | 2.5 |
| Liquid paraffin | 2.5 |
| Ethanol | 5.0 |
| Methylparaben | 0.1 |
| Fragrance | 0.1 |
| LPG (4.0 kg/cm$^2$ · G, 20° C.) | 10.0 |
| Water | balance |
| total | 100 wt % |

Japanese Patent Application No. 164308/1998 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A silicone emulsion comprising a carboxyl-bearing organopolysiloxane of formula (1):

$$R^1_xR^2_yR^3_zSiO_{(4-x-y-z)/2} \quad (1)$$

wherein $R^1$ is a monovalent hydrocarbon group having 1 to 20 carbon atoms, $R^2$ is as defined for $R^1$ or an OX group wherein X is hydrogen or a monovalent hydrocarbon group having 1 to 6 carbon atoms, $R^3$ is a —$R^4$COOH group wherein $R^4$ is a divalent hydrocarbon group having 1 to 20 carbon atoms, x, y, and z are numbers satisfying $0<x\leq2$, $0\leq y<0.05$, $0<z\leq0.15$, and $1.8<x+y+z<2.2$, said organopolysiloxane containing at least one carboxyl group in the molecule, having a degree of polymerization of 200 to 20,000, and being obtained by emulsion plymerization, said organopolysiloxane of formula (1) including (A) structural units of the following average unit formula (2):

$$R^1_aR^2_bSiO_{(4-a-b)/2} \quad (2)$$

wherein $R^1$ and $R^2$ are defined above, a and b are numbers satisfying $0<a\leq3$, $0\leq b<3$, and $1\leq a+b\leq3$, (B) structural units of the following average unit formula (3):

$$R^3_cR^2_dSiO_{(4-c-d)/2} \quad (3)$$

wherein $R^2$ and $R^3$ are as defined above, c and d are numbers satisfying $0<c\leq3$, $0\leq d<3$, and $1\leq c+d\leq3$, (C) structural units of the following average unit formula (4)

$$R^1SiO_{3/2} \quad (4)$$

wherein $R^1$ is as defined above,
in a molar ratio (A):(B):(C) of 1: (0.0001 to 0.01): (0 to 0.01).

2. A method for preparing the carboxyl-bearing silicone emulsion of claim 1, comprising emulsion polymerizing a mixture of organopolysiloxanes in water in the presence of an anionic surfactant for emulsion polymerization, and neutralizing the resulting reaction mixture, said mixture of organopolysiloxanes comprising (A) an organopolysiloxane of the following general formula (2a):

$$R^1_a R^2_b SiO_{(4-a-b)/2} \quad (2a)$$

wherein $R^1$ and $R^2$ are as defined above, a and b are numbers satisfying $0<a\leq 3$, $0\leq b<3$, and $1\leq a+b\leq 3$, (B) an organopolysiloxane of the following general formula (3a):

$$R^3_c R^2_d SiO_{(4-c-d)/2} \quad (3a)$$

wherein $R^2$ and $R^3$ are as defined above, c and d are numbers satisfying $0<c\leq 3$, $0\leq d<3$, and $1\leq c+d\leq 3$, and, (C) an organosilane of the following general formula (4a):

$$R^1 Si(OX)_3 \quad (4a)$$

wherein $R^1$ and X as defined above, or a partial hydrolytic condensate thereof.

3. A method for preparing the carboxyl-bearing silicone emulsion of claim 1, comprising emulsifying and dispersing a mixture of organopolysiloxanes in water in the presence of a nonionic or anionic surfactant, emulsion polymerizing the organopolysiloxanes in the presence of a polymerization catalyst, and neutralizing the resulting reaction mixture, said mixture of organopolysiloxanes comprising (A) an organopolysiloxane of the following general formula (2a):

$$R^1_a R^2_b SiO_{(4-a-b)/2} \quad (2a)$$

wherein $R^1$ and $R^2$ are as defined above, a and b are numbers satisfying $0<a\leq 3$, $0\leq b<3$, and $1\leq a+b\leq 3$, (B) an organopolysiloxane of the following general formula (3a):

$$R^3_c R^2_d SiO_{(4-c-d)/2} \quad (3a)$$

wherein $R^2$ and $R^3$ are as defined above, c and d are numbers satisfying $0<c\leq 3$, $0\leq d<3$, and $1\leq c+d\leq 3$, and, (C) an organosilane of the following general formula (4a):

$$R^1 Si(OX)_3 \quad (4a)$$

wherein $R^1$ and X as defined above, or a partial hydrolytic condensate thereof.

4. A hair preparation comprising the silicone emulsion of claim 1.

5. A method of preparing a hair preparation according to claim 4, comprising mixing the silicone emulsion with conventional hair preparation ingredients.

6. A method according to claim 5, wherein the ingredients are pearling agents, emulsifiers, fragrance, pigments, preservatives, antioxidants, thickeners, dandruff control agents, antibacterial agents, anti-inflammatory agents, vitamins, or UV absorbers.

7. The silicone emulsion of claim 1, wherein $R^1$ is methyl, ethyl, propyl, butyl, octyl, lauryl, stearyl, vinyl, allyl, phenyl, tolyl, naphthyl, 2-phenylethyl, cyclopentyl or cyclohexyl, each optionally substituted by halogen, cyano or mercapto.

8. The silicone emulsion of claim 1, wherein X is methyl, ethyl, propyl, butyl, vinyl, allyl or phenyl, each optionally substituted by halogen, cyano or mercapto.

9. The silicone emulsion of claim 1, wherein $R^3$ is methylene, ethylene, trimethylene, tetramethylene, hexamethylene or phenylene.

10. The silicone emulsion of claim 1, wherein $1.8\leq x\leq 2$, $0\leq y<0.05$.

11. The silicone emulsion of claim 1, wherein $0\leq y\leq 0.01$, $0<z\leq 0.15$.

12. The silicone emulsion of claim 1, wherein $0.01\leq z\leq 0.05$, and $1.8<x+y+z<2.2$.

13. The silicone emulsion of claim 1, wherein $1.81\leq x+y+z\leq 2.06$.

14. The silicone emulsion of claim 1, wherein A is $(CH_3)_2 SiO$, $(CH_3)(C_6H_5)SiO$, $(C_6H_5)_2 SiO$, $(C_2H_5)_2 SiO$, $(CH_3)(C_2H_5)SiO$, $(C_3H_7)_2 SiO$ or $(CH_3)(C_3H_7)SiO$.

15. The silicone emulsion of claim 1, wherein B is $(CH_3)(HOOCC_2H_4)SiO$, $(CH_3)(HOOCC_3H_6)SiO$ or $(CH_3)(HOOCC_{11}H_{22})SiO$.

16. The silicone emulsion of claim 1, wherein C is $CH_3 SiO_{3/2}$, $C_6H_5 SiO_{3/2}$, $C_2H_5 SiO_{3/2}$ or $C_3H_7 SiO_{3/2}$.

* * * * *